(12) United States Patent
Neale

(10) Patent No.: US 9,968,746 B2
(45) Date of Patent: May 15, 2018

(54) NEEDLE PROTECTION ASSEMBLY WITH RADIALLY MOVABLE LOCKING ELEMENT

(71) Applicant: BECTON DICKINSON FRANCE, Le Pont de Claix (FR)

(72) Inventor: Kevin David Neale, Swindon (GB)

(73) Assignee: Becton Dickinson France, Le Pont-de-Claix (FR)

( * ) Notice: Subject to any disclaimer, the term of this patent is extended or adjusted under 35 U.S.C. 154(b) by 893 days.

(21) Appl. No.: 13/625,047

(22) Filed: Sep. 24, 2012

(65) Prior Publication Data

US 2013/0018312 A1 Jan. 17, 2013
US 2018/0050162 A9 Feb. 22, 2018

Related U.S. Application Data

(63) Continuation of application No. 13/368,488, filed on Feb. 8, 2012, now abandoned, which is a continuation
(Continued)

(30) Foreign Application Priority Data

Apr. 16, 2008 (FR) ..................................... 08 02103

(51) Int. Cl.
*A61M 5/32* (2006.01)
(52) U.S. Cl.
CPC ........... *A61M 5/326* (2013.01); *A61M 5/3202* (2013.01); *A61M 2005/3247* (2013.01)

(58) Field of Classification Search
CPC ............ A61M 5/50; A61M 2005/3247; A61M 2005/3267; A61M 5/3243; A61M 5/3219;
(Continued)

(56) References Cited

U.S. PATENT DOCUMENTS

| 4,813,940 A | 3/1989 | Parry |
| 2004/0102740 A1 | 5/2004 | Meloul |

(Continued)

FOREIGN PATENT DOCUMENTS

| WO | 91/17783 A1 | 11/1991 |
| WO | 2004000397 A1 | 12/2003 |
| WO | WO 2009144549 | * 12/2009 |

*Primary Examiner* — Matthew F Desanto
(74) *Attorney, Agent, or Firm* — The Webb Law Firm

(57) ABSTRACT

The application relates to needle protection assembly (1)) comprising:—a support (2) of the needle (3),—a needle shield (8) having a longitudinal axis A,—urging means (13) for displacing said needle shield (8) from a "in, use" position to a "after use" position,—a locking element (10) intended to prevent said needle shield (8) from moving back from its "after use" position to its "in use" position, characterized in that said locking element (10) has a longitudinal axis B and is radially movable with respect to said needle shield (8) between a "free" position, in which the longitudinal axis A of the needle shield (8) and the longitudinal axis B of the locking element (10) are merged and in which said needle shield (8) is movable from its "in use" position to its "after use" position, and a "locking position", in which the longitudinal axis B is radially spaced apart from the longitudinal axis A and in which movement of the needle shield (8) from its "after use" position to its "in use" position is prevented.

19 Claims, 6 Drawing Sheets

Figure 1:
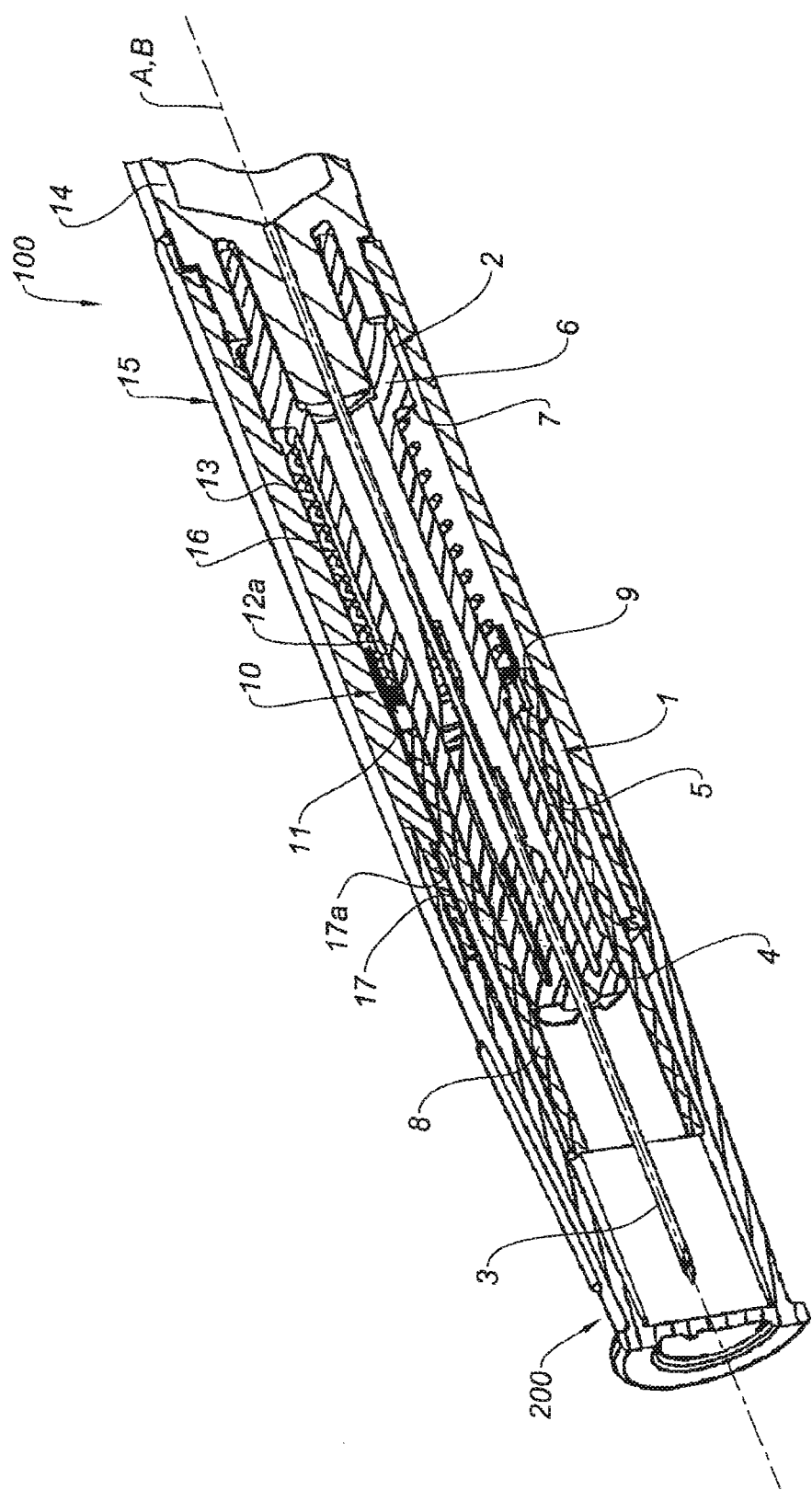

Related U.S. Application Data of application No. 12/988,170, filed as application No. PCT/IB2009/005532 on Apr. 14, 2009, now abandoned.

(58) Field of Classification Search
CPC ........ A61M 5/3245; A61M 2005/3249; A61M 2005/3252; A61M 5/3271; A61M 5/326
USPC .................................. 604/110, 192–198, 263
See application file for complete search history.

(56) References Cited

U.S. PATENT DOCUMENTS

| | | |
|---|---|---|
| 2005/0113750 A1 | 5/2005 | Targell |
| 2005/0277893 A1* | 12/2005 | Liversidge .................... 604/198 |
| 2006/0189933 A1* | 8/2006 | Alheidt et al. ................ 604/110 |

\* cited by examiner

NEEDLE PROTECTION ASSEMBLY WITH RADIALLY MOVABLE LOCKING ELEMENT

This application is a continuation of U.S. patent application Ser. No. 13/368,488, filed on Feb. 8, 2012, now pending, which is a continuation of U.S. patent application Ser. No. 12/988,170, filed on Oct. 15, 2010, now pending, which is a National Stage Application under 35 U.S.C. § 371 of PCT Application No. PCT/IB2009/005532, filed Apr. 14, 2009, the contents of these applications being incorporated by reference herein.

The present invention relates to a needle protection assembly that is to be connected to an injection device such as a syringe in view of completing an injection, said needle protection assembly being triggered after the injection in order to protect the user from accidental needle stick injuries and prevent needle re-use.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

In the medical field, it is usual to provide injection devices with needle protection systems in order to prevent the needle to be reached by the user or the patient before and/or after use of the injection device, in view of limiting accidental needle stick injuries. In addition, such needle protection systems also enable to prevent re-use of the injection devices.

Usually, the needle protection systems include a needle shield able to move distally over the needle once the injection is completed. The distal movement of the needle shield with respect to the needle is often triggered by a spring in an automatic way when the needle is withdrawn from the injection site. In general, the needle shield is then locked in its "after use" position thanks to a locking system, most of the time based on the cooperation of deflecting members located either on the needle hub and/or on the needle shield.

The document US2005/0113750 discloses such a needle protection system in which the locking system comprises a spring urging a needle shield toward its "after use" position and a deflecting leg provided on the needle shield, the deflecting leg being engaged into a groove provided on the needle hub in the "after use" position.

Nevertheless, the needle protection systems of the prior art have the drawback that, because of the energy necessary to deflect the deflecting members, the spring force must be high in order to displace the needle shield and overcome the deflecting members resistance. This has the consequence that, in "storage" position, before use, the high spring force of the compressed spring may deform the usual plastic parts forming the needle assembly and/or the injection device. This deformation may cause the needle protection system not to work properly at the time of use. This deformation may also cause wrong depth injection at the time of injection. Indeed, during the injection, the high spring force will push the needle shield against the skin, generating a push back force on the injection device proportional with the high force of the spring. This push back force will render difficult and unpredictable the accurate positioning of a constant pressure on the skin and make the injection operation more difficult to perform. In addition, springs with high force are more cumbersome, expensive and difficult to assemble than low duty spring. On the other side, low duty springs do not apply enough force to be able to overcome the deflecting members resistance and allow the needle protection system to work properly.

WO91/17783 discloses an injection device provided with a needle shield that becomes misaligned with the needle hub in its "after use" position. Nevertheless, the injection device of WO91/17783 requires a manual rotation of a part of the injection device to put the needle shield in its "after use" position. Such an injection device is therefore not easy to handle.

US2004/0102740 discloses an injection device provided with a needle shield with a locking element that is displaced when the needle shield moves in its "after use" position. Nevertheless, the locking element of US2004/0102740 is in direct contact with the needle and particularly with the needle distal tip when the needle shield is moved to its "after use" position. Such a direct contact is not desirable as it exerts a continuous force on the needle therefore rendering the injection step less reliable. Moreover, such a direct contact may also cause the spilling of liquid medicine or blood. Indeed, at the end of the injection, some liquid medicine or blood may be present at the distal tip of the needle and spilled of, at the time the needle shield moves to its "after use" position, such a spilling phenomenon being likely to cause contamination risks. In addition, it appears that in US2004/0102740, in order to prevent the locking element from being pierced by the needle when in its "after use" position, the locking element should be made of a specific material such as metal. This may cause the injection device to be expensive to produce and therefore to purchase. In this example of the prior art as described in US2004/0102740, the needle shield is made of several parts telescopically assembled, the locking element is maintained in an initial position by the needle resisting against a biasing force exerted by a spring. Assembling such parts as described above may be particularly difficult in term of industrial process and the reliability of such process may be highly questionable. The activation of such needle shield, in order to have it moved from its "in use" position to its "after use" position, is obtained by the user manually triggering a lateral push button freeing the extension of the telescopically movable parts of the needle shield. Such injection devices are therefore generally uneasy to use moreover, as these devices are not automatically protected, the risk of needle stick injuries after their use may be important.

Moreover, the needle protection systems of the prior art necessitate a plurality of different parts, in particular parts forming the locking system, and are therefore difficult and long to manufacture.

There is therefore a need for a needle protection assembly, that would be easily triggered at the end of injection in order to avoid accidental needle stick for the user and re-use of the needle, and at the same time that would not be likely to cause the deformation of the plastic parts forming the needle assembly during storage, and that would be easy to assemble. There is also the need of a needle protection assembly limiting the risk of liquid spilling from the needle after the end of the injection. Furthermore, there is a need of a needle protection assembly, easy to assemble with a limited number of parts, for example made of plastic and that are not particularly expensive to manufacture.

The present invention remedies to this problem by providing a needle protection assembly comprising a specific locking system so that the urging means, such as a spring, used to cause the distal movement of the protection at the end of injection is a low duty urging means that does not need to show a too high force, such a needle protection assembly being preferably easy to manufacture and preventing the spilling of the needle tip after the injection.

A first aspect of the present invention is a needle protection assembly intended to protect the needle of a needle assembly, said needle protection assembly comprising at least:

a support intended to be fixed relative to said needle,
a needle shield intended to receive at least part of said needle, said needle shield having a longitudinal axis A and being axially movable with respect to said support between at least an "in use" position in which said needle shield is intended to leave a portion of said needle uncovered, and an "after use" position in which said needle shield is intended to cover said needle,
urging means tending to displace said needle shield from said "in use" position to said "after use" position,
a locking element intended to prevent said needle shield from moving back from its "after use" position to its "in use" position,
characterized in that said locking element has a longitudinal axis B and is radially movable with respect to said needle shield between at least a "free" position, in which the longitudinal axis A of said needle shield and the longitudinal axis B of said locking element are co-axial with each other and in which said needle shield may be moved from its "in use" position to its "after use" position, and a "locking" position, in which the longitudinal axis B of said locking element is radially spaced apart from the longitudinal axis A of said needle shield and in which movement of said needle shield from its "after use" position to its "in use" position is prevented, said needle being free from any contact with said locking element at least when said needle shield moves from its "in use" position to its "after use" position.

In the needle protection assembly of the invention, the urging means, for example a helical spring, is used to cause the movement of the needle shield once the injection is completed but it does not have to overcome the friction force opposed by deflecting members of the locking systems of the prior art or any point of resistance to lock the needle shield in its "after use" position. It is the fact that the needle shield and the locking element are no more coaxial in the "after use" position of the needle shield that locks the needle shield in said "after use" position. Less force is required from the urging means, such as the helical spring, of the needle protection assembly of the invention. In consequence, the urging means of the needle protection assembly of the invention, even in the "storage" position, do not exert a high force on the plastic parts forming the assembly. The risks of deformation of these plastic parts are therefore limited with the needle protection assembly of the invention. In addition, a weaker spring than the springs used in the devices of the prior art may be used as urging means in the needle protection assembly of the invention.

Moreover, in the needle protection assembly of the invention, the needle does not interfere in the cooperation between the locking element and the needle shield when the needle shield is moved from its "in use" position to its "after use" position. As a consequence, the locking element does not enter in contact with the needle when the needle shield is moved from its "in use" position to its "after use" position. With the needle protection assembly of the invention, risks of spilling of liquid medicine or of blood, that could be present at the end of the injection at the distal tip of the needle, are limited.

In particular, the needle of the needle protection assembly of the invention is not submitted to urging or biasing forces when the needle protection assembly is in a "storage" position. It is neither submitted to such forces during the use of the needle protection assembly with an injection device. As a consequence, the injection is step is more reliable and more efficient with the needle protection assembly of the invention than with an assembly of the prior art where the needle is submitted to a spring force for example.

The needle protection assembly of the invention is therefore easier to manufacture than assemblies of the prior art.

In an embodiment of the needle protection assembly of the invention, in its "locking" position, said locking element is axially locked in the proximal direction, by means of at least part of the proximal end of said locking element resting against at least one abutment provided on said support.

For example, in an embodiment, said locking element is located between said urging means and said needle shield, said locking element and said needle shield being coupled to said urging means when said locking element is in its "free" position, said locking element and needle shield being decoupled from said urging means when said locking element is in its "locking" position. By "coupled" is meant in the present application that the locking element and the needle shield are linked to the urging means: for example, the urging means may be in contact with said locking element which is itself in contact with said needle shield. As a consequence, when said urging means apply a force on said locking element, the force is transferred to the needle shield. By opposition, by "decoupled" is meant in the present application that the locking element and needle shield are no more dependent on the urging means.

In an embodiment, the needle protection assembly of the invention further comprises guiding means intended to maintain said locking element in alignment with said needle shield in the "in use" position of said needle shield and preventing said locking element to move toward its "locking" position. The needle shield and the locking element are therefore coaxial during the "in use" position of the needle shield.

In an embodiment, at least part of said needle shield has the global shape of a tube and at least part of said locking element having the global shape of a ring of radial dimensions substantially similar to that of the tube.

In an embodiment of the needle protection assembly of the invention, the support further comprises an outer sleeve located around the needle shield and the locking element, and an inner core received within said needle shield and said locking element, said needle shield and locking element being movable together in translation along said axis A and B with respect to said outer sleeve and to said inner core at least in the "in use" position of said needle shield. The guiding means may be provided on at least one of said inner core or said outer sleeve. Furthermore, the guiding means may comprise a longitudinal rib respectively provided on part of the length of the inner wall of said outer sleeve or on part of the length of the outer wall of said inner core, at least part of a wall of said ring bearing on said longitudinal rib in the "in use" position of the needle shield. In such an embodiment, the longitudinal rib maintains the locking element coaxial with the needle shield.

In an embodiment, the needle protection assembly further comprises directing means designed for causing the radial displacement of said locking element with respect to said needle shield under the action of said urging means when said needle shield reaches its "after use" position, thereby causing said locking element to move from its "free" position to its "locking position".

In an embodiment of the invention, a first part of said directing means is located on said locking element and a second part of said directing means is located on said needle shield, said first and second parts of said directing means cooperating together so as to cause the radial displacement of said locking element with respect to said needle shield under the action of said urging means when said needle shield reaches its "after use" position.

For example, said first part of said directing means comprises an angled surface located on the ring and said second part of said directing means comprises a complementary angled surface located on the tube, said angled surface and complementary angled surface being in regard to each other and sliding on each other so as to cause the radial displacement of said locking element with respect to said needle shield under the action of said urging means when said needle shield reaches its "after use" position. For example, at least one of said angled surface or complementary angled surface is provided with at least one spine extending inwardly and radially, said at least one spine contributing to increase the surface contact between said angled surface and said complementary angled surface when they slide on each other. In such an embodiment, it is preferred that the friction at the surface contact between the ring and the tube be low to ensure better radial displacement of the ring with respect to the tube.

In an embodiment of the invention, said outer sleeve comprises on its inner wall a recess located in alignment with said longitudinal rib, said at least part of a wall of said ring bearing on said longitudinal rib in the "in use" position of the needle shield being caused to engage said recess by radial displacement of said locking element with respect to said needle shield when said needle shield reaches its "after use" position under the action of said urging means, said recess being provided with said abutment.

In an embodiment, said urging means comprise at feast a helical spring.

In an embodiment, said needle shield is axially movable with respect to said support between a "before use" position, in which said needle shield covers at least part of the needle, and said "in use" position.

In an embodiment, the needle protection assembly comprises a cam, located on said needle shield or on said support, and a peg, respectively located on said support or on said shield, said cam and said peg being designed so as to cooperate together for defining at least one of said "in use" position and/or said "before use" and/or said "after use" position of the needle shield.

Another aspect of the invention is a needle assembly comprising at least a needle hub provided with a needle wherein it further comprises a needle protection assembly as described above.

Another aspect of the invention is an injection device comprising at least a needle assembly and a reservoir, wherein it further comprises a needle protection assembly as described above.

Figure 2:
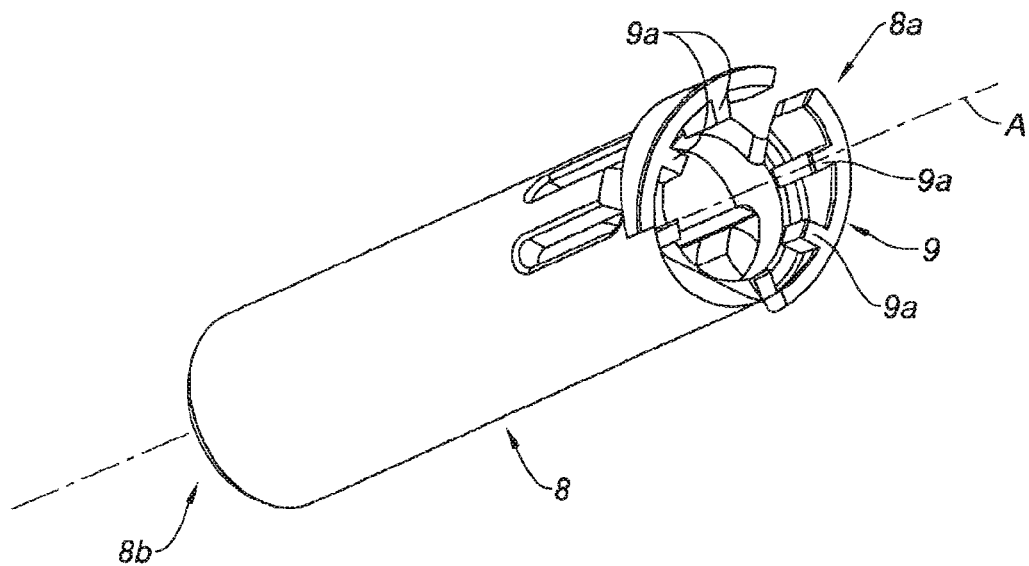
Figure 3:
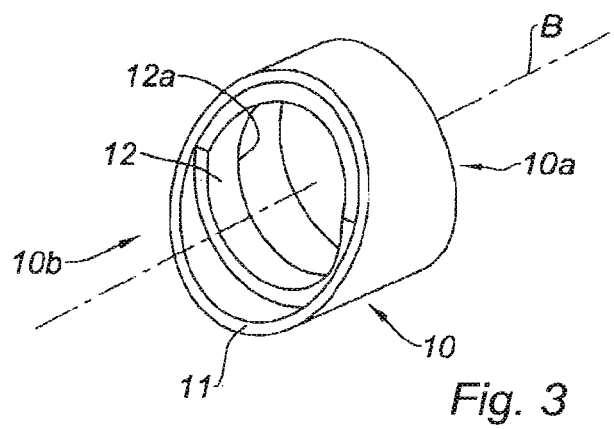
Figure 4:
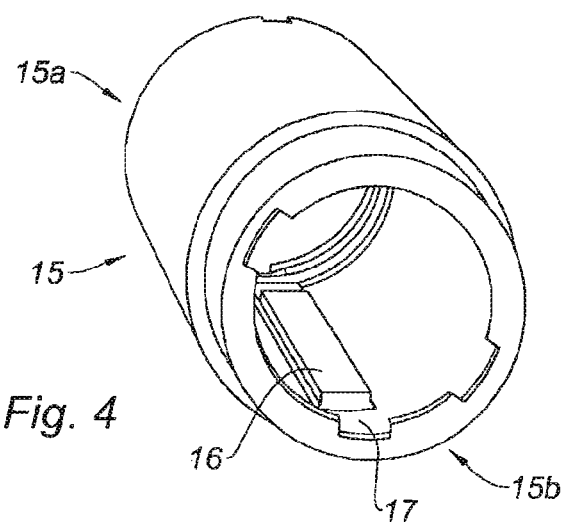
Figure 5:
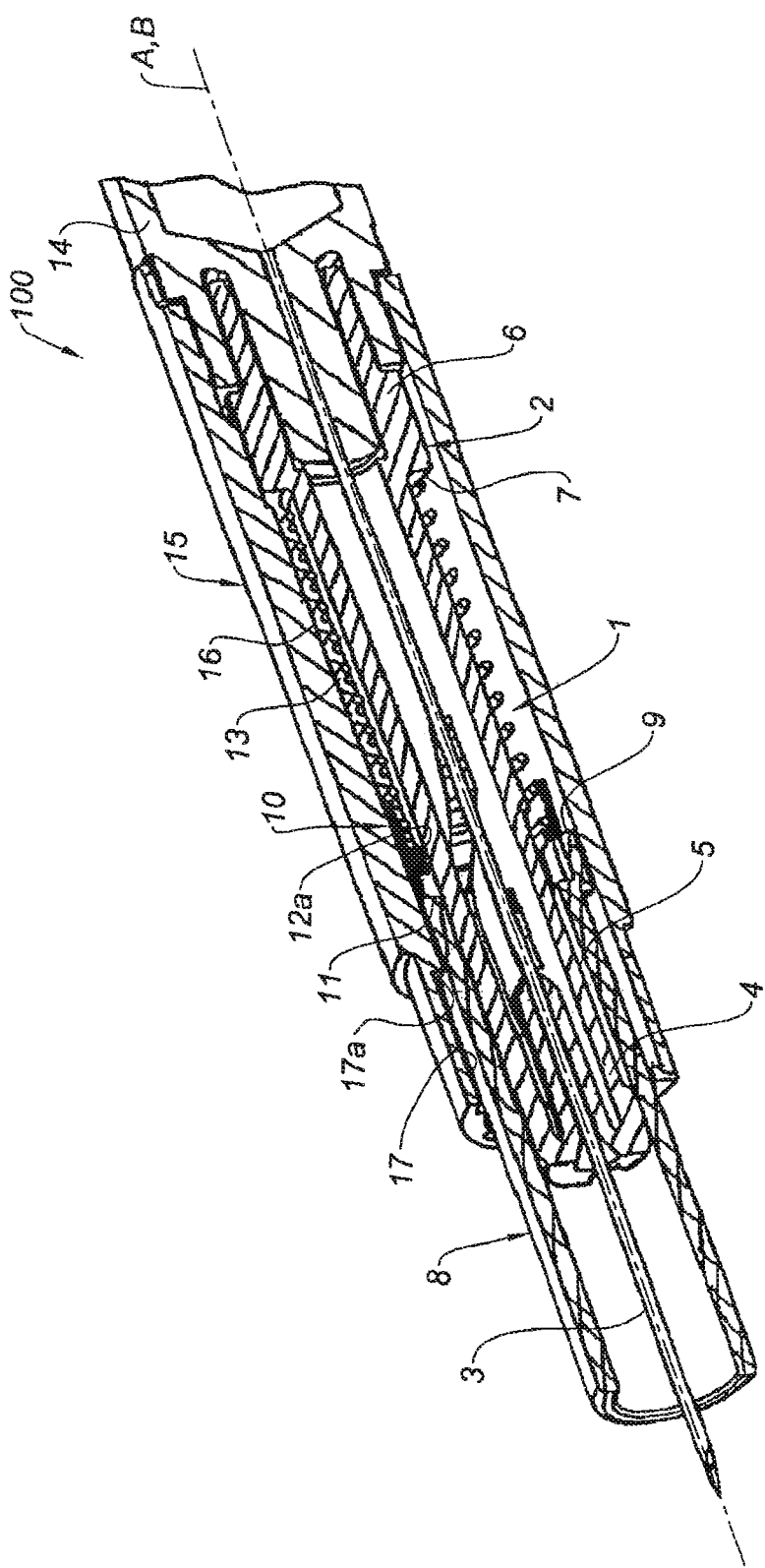
Figure 6:
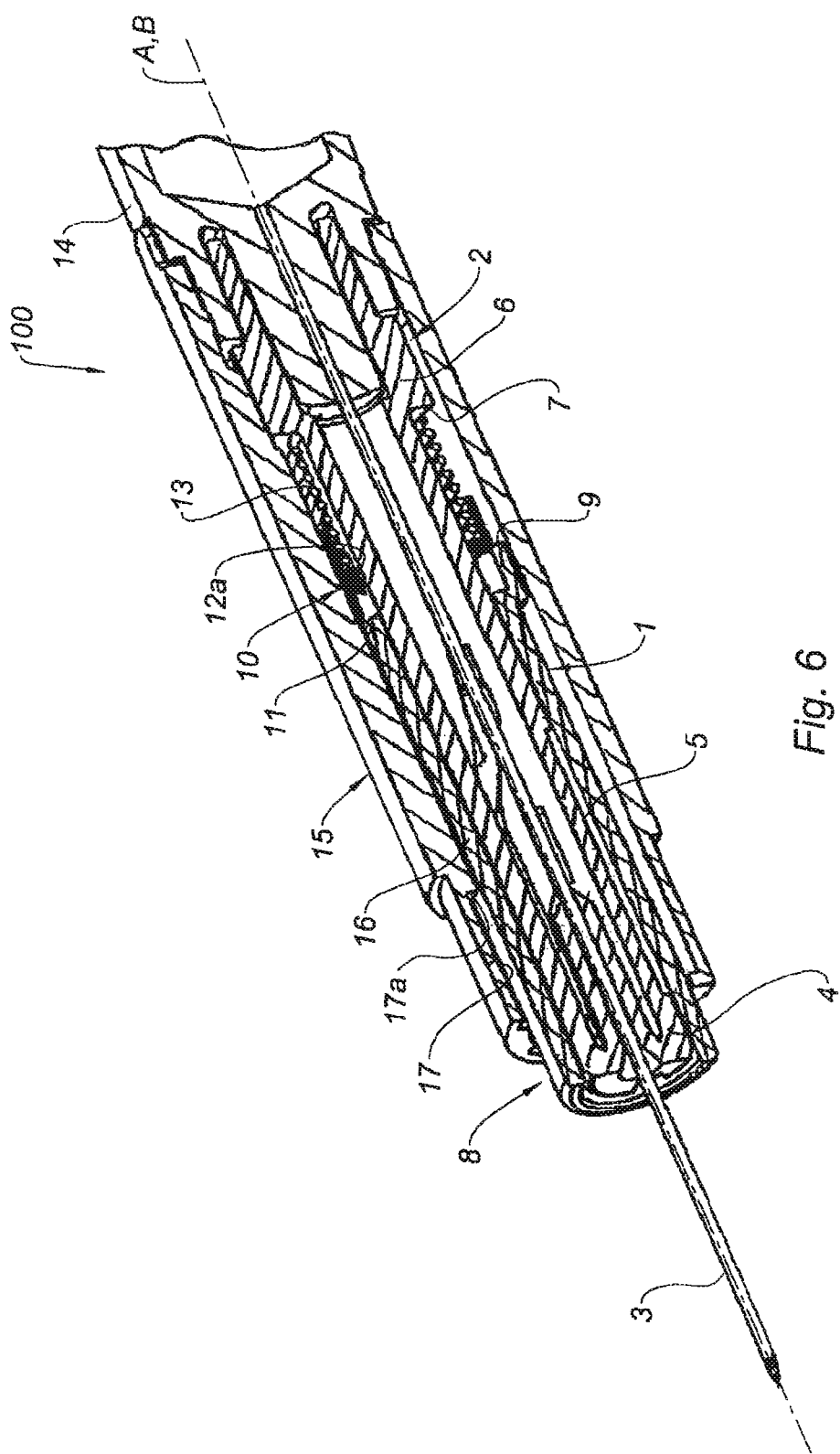
Figure 7:
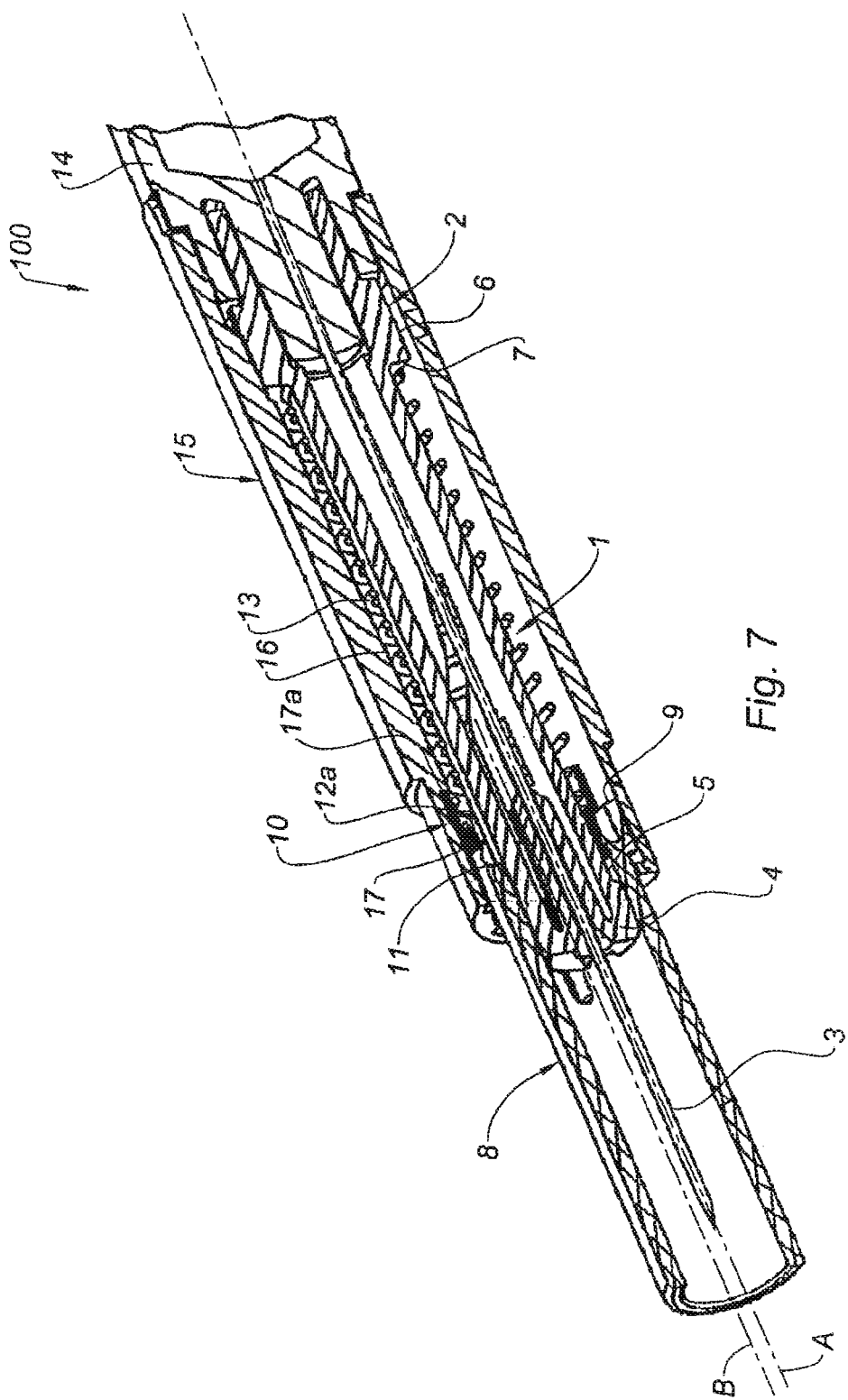

The needle protection assembly, needle assembly and injection device of the invention will now be further described in reference to the following description and attached drawings in which:

FIG. 1 is a cross section view of an injection device comprising a needle protection assembly according to the invention, in a "storage" position, said injection device being provided with a protection cap, FIG. 2 is a perspective view of the needle shield of the needle protection assembly of FIG. 1, FIG. 3 is a perspective view of the locking element of the needle protection assembly of FIG. 1, FIG. 4 is a perspective view of the outer sleeve of the needle protection assembly of FIG. 1, FIG. 5 is a cross section view of the injection device of FIG. 1, in a "before use" position, once the protection cap has been removed, FIG. 6 is a cross section view of the injection device of FIG. 1 during injection, namely in an "in use" position, FIG. 7 is a cross section view of the injection device of FIG. 1 in an "after use" position, right at the end of the injection, FIGS. 8A to 8D are partial views of the needle protection assembly of the injection device of FIGS. 1-7 showing the peg position in the cam, respectively in the following positions: "storage", "before use", "in use" and "after use", In reference to FIG. 1 is shown a needle protection assembly 1 according to the invention, mounted on an injection device 100 (partially shown). The injection device 100 is in a "storage" position and its distal end is covered with a protection cap 200. The needle protection assembly 1 of the invention comprises a support 2 that bears a needle 3. The support 2 comprises an inner core 4, said inner core 4 comprising on its outer wall a longitudinal cut 5. The support 2 also comprises a proximal part 6 of outer diameter larger than the outer diameter of the inner core 4 and forming with respect to said inner core 4 a rim 7. As shown on FIGS. 8A to 8D, the outer wall of the support 2, for example the outer wall of the inner core 4, is provided with a longitudinal cam 4a having the global shape of a V, the function of which will be explained later.

The needle protection assembly 1 of FIG. 1 also comprises a needle shield 8 receiving at least partially said support 2 and in particular said inner core 4 of said support 2. With reference to FIG. 2, the needle shield 8 has the global shape of a tube having a longitudinal axis A. The needle shield 8 is open at its proximal end 8a and at its distal end 8b. Its proximal end 8a is under the form of a first angled surface 9, said first angled surface 9 being provided with a plurality of spines 9a extending inwardly and radially, the function of which will be explained later. As shown on FIGS. 8A to 8D, the needle shield 8 is provided with a peg 8c (not visible on FIG. 2) able to cooperate with the cam 4a so as to define respectively a "before use", a "in use" and a "after use" positions of the needle shield 8. These positions are described hereafter. For sake of clarity, the needle shield 8 is not shown on FIGS. 8A-8B only the peg 8c, which is part of said needle shield 8, is shown on these figures.

As will appear clearly from the description of FIGS. 5-7, the needle shield 8 is axially movable with respect to the support 2 between a "before use" position, in which said needle shield 8 covers at least part of the needle 3, as shown on FIG. 5, an "in use" position in which said needle shield 8 leaves a portion of said needle 3 uncovered, as shown on FIG. 6, and an "after use" position in which said needle shield 8 covers said needle 3, as shown on FIG. 7.

The needle protection assembly 1 of FIG. 1 further comprises a ring 10 surrounding the inner core 4 of the support 2, said ring 10 being located adjacent to the proximal end 8a of the needle shield 8. The ring 10 is shown on FIG. 3. As shown on this figure, the ring 10 has a longitudinal axis B and is open at its proximal end 10a and at its distal end 10b. The distal end 10b of the ring 10 is under the form of a second angled surface 11. The first angled surface 9 of the needle shield 8 and the second angled surface 11 of the ring 10 have the same angle and are therefore complementary.

As shown on FIG. 3, the inner wall of the ring 10 is provided with an annular rim 12 forming a proximal abutment surface 12a.

The respective radial dimensions of the tube forming the needle shield 8 and of the ring 10 are substantially similar.

With reference to FIG. 1, the distal end of the ring 10 faces the proximal end 8a (see FIG. 3) of the needle shield 8, and in this position, the first angled surface 9 of the needle shield 8 is in tight and complementary contact with the second angled surface 11 of the ring 10. As appears also from FIG. 1, in this position, the needle shield 8 and the ring 10 are coaxial, their respective longitudinal axis A and B being merged. As a remark, on this figure, the longitudinal axis A and B are also merged with the longitudinal axis of the injection device 100. In other words, the needle shield 8 and the ring 10 are in alignment with each other.

The needle protection assembly 1 of FIG. 1 further comprises a helical spring 13, located between the support 2 and the ring 10. On the example shown on FIG. 1, the proximal end of the helical spring 13 bears on the rim 7 and its distal end bears on the proximal abutment surface 12a of the annular rim 12 of the ring 10. In the "storage" position shown on FIG. 1, the helical spring 13 is in a partially expanded state. As will appear later in the detailed description of the operation of the injection device 100, the helical spring 13 acts as urging means for displacing the needle shield 8 from its "in use" position to its "after use" position.

As appears from FIG. 1, the ring 10 is located between the helical spring 13 and the needle shield 8. Moreover, the helical spring 13 is in contact with the ring 10 and the ring 10 is in contact with the needle shield 8. As a consequence, the ring 10 and the needle shield 8 are coupled to the helical spring 13: in other words, a proximal force exerted on the needle shield 8 will cause the compression of the helical spring 13. On the contrary, the extension of the helical spring 13 will cause the distal movement of both the ring 10 and the needle shield 8.

The injection device 100 of FIG. 1 also comprises a barrel 14 (partially shown) intended to receive a product to be injected and an outer sleeve 15 receiving said barrel 14 and the needle protection assembly 1.

In the example as shown, the outer sleeve 15 is fixed with respect to the support 2 and therefore forms part of the support 2. As appears from the figures, the outer sleeve 15 receives the ring 10 and the needle shield 8.

The outer sleeve 15 is shown on FIG. 4. As shown on this figure, the outer sleeve 15 has a general cylindrical shape and is open at its proximal end 15a and at its distal end 15b. The outer sleeve 15 is provided on part of the length of its inner wall with a longitudinal rib 16, said longitudinal rib 16 not extending up to the distal end 15b of the outer sleeve 15. The distal part of the inner wall in alignment with said longitudinal rib 16, and free of said longitudinal rib 16, defines a recess 17 provided at its proximal end with an abutment 17a.

As shown on FIG. 1, in the "storage" position of the injection device 100, the at least part of the wall of the ring 10 bears radially on the rib 16 of the outer sleeve 15. As already said, the ring 10 is therefore coaxial with the needle shield 8 and said rib 16 acts as guiding means for maintaining the ring 10 in alignment with the tube forming the needle shield 8.

The operation of the needle protection assembly 1 and of the injection device 100 will now be explained in reference to FIGS. 1 and 5-7.

On FIG. 1, the injection device 100 is in a "storage" position. The distal end of the injection device 100 is covered with a protection cap 200 in order to avoid accidental needle stick injury for any person having to handle the injection device 100. As shown on FIG. 8A, the peg 8c is in a "free" position in a first branch of the V-shaped cam 4a.

In order to proceed with the injection, the user removes the protection cap 200 as shown on FIG. 5. In this "before use" position shown on FIG. 5, the needle shield 8 covers part of the needle 3. In an example not shown, the needle shield 8 could cover the entire needle 3 so as to prevent any accidental needle stick injury in this position.

Figure 8A:
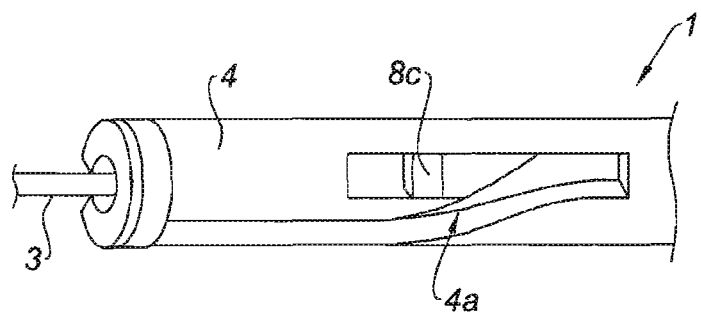
Figure 8B:
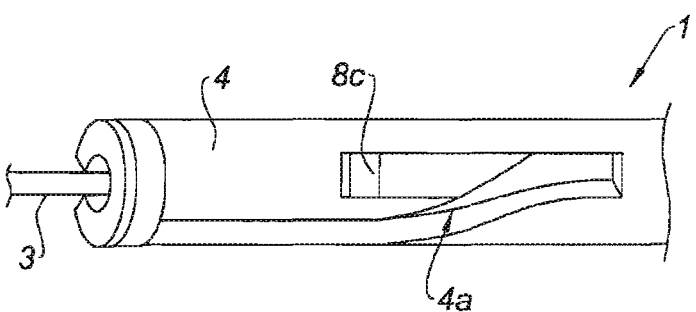
Figure 8C:
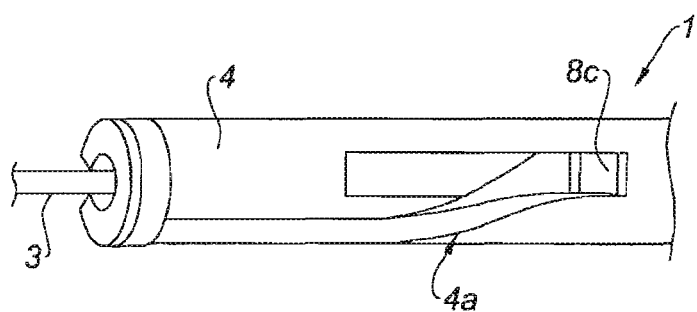

In the position shown on FIG. 5, the helical spring 13 is in a slightly less compressed state than in FIG. 1, namely in a partially expanded state and, as shown on FIG. 8B, the peg 8c abuts in the free extremity of the first branch of the cam 4a. In this "before use" position shown on FIG. 5, the longitudinal axis A of the needle shield 8 and the longitudinal axis B of the ring 10 are coaxial with each other, ie merged. The needle shield 8 and the ring 10 are in alignment with each other.

The user then applies the injection device 100 on the skin of a patient (not shown), inserts the needle 3 into the injection site until the distal end 8b (see FIG. 3) of the needle shield 8 comes in contact with the skin. In order to fully insert the needle 3 in the site of injection, the user then exerts a distal pressure on the injection device 100, this having as a consequence to cause the distal movement of the support 2 with respect to the needle shield 8, as shown on FIG. 6, said needle shield 8 being blocked against the skin of the patient (not shown). During the distal movement of the support 2, the rim 7 has come closer to the ring 10 and the helical spring 13 is now in a compressed state, as shown on FIG. 6. As shown on FIG. 8C, the peg 8c is then in abutment on the junction point of the two branches forming the V-shaped cam 4a. The needle shield 8 is in its "in use" position. The user may then realise the injection of the product to be injected.

In this "in use" position of the needle shield 8 as shown on FIG. 6, the longitudinal axis A of the needle shield 8 and the longitudinal axis B of the ring 10 are co-axial with each other, ie merged. The needle shield 8 and the ring 10 are in alignment with each other.

Once the injection step (not shown) is completed, the user removes the injection device 100 from the injection site and the needle shield 8 is no more blocked by the skin of the patient. The helical spring 13 is therefore free to return to its expanded state and it causes the distal movement of both the ring 10 and the needle shield 8 with respect to the support 2 as shown on FIG. 7. The needle shield 8 deploys and covers the needle 3, thereby preventing any accidental needle stick injury for the user and any re-use of the injection device 100. During this step, the helical spring 13 acts as urging means tending to displace the needle shield 8 from its "in use" position to its "after use" position.

While expanding, the helical spring 13 has pushed the ring 10 distally and axially, together and coaxially with the needle shield 8. During this distal displacement, the ring 10 has been maintained coaxial with the needle shield 8 thanks to the longitudinal rib 16 on which part of the wall of the ring 10 is bearing. As the needle shield 8 reaches its "after use" position", the ring 10 reaches the end of the longitudinal rib 16. In consequence, the part of the wall of the ring 10 which was bearing on the longitudinal rib 16 is urged to move radially with respect to said needle shield 8 due to the first and second angled surfaces (9, 11) cooperating together by sliding with respect to each other, thereby forcing said part of the wall of the ring 10 into the recess 17, and under the action of the helical spring 13 which engages the longitudinal cut 5 provided on the outer wall of the inner core 4 of the support 2. While said first and second angled surfaces (9, 11) slide with respect to each other, the spines 9*a* provided on the first angled surface 9 contribute to increase the surface contact between the first and second angled surfaces (9, 11) and facilitate the sliding of said two angled surfaces with respect to each other. The first and second angled surfaces (9, 11) have therefore acted as directing means for causing the radial displacement of the ring 10 with respect to the needle shield 8. In order to ensure smoother radial displacement of the ring 10 with respect to the needle shield 8, it is preferred that the friction forces between the ring 10 and the needle shield 8 be as low as possible.

As shown on FIG. 7, the part of the wall of the ring 10 which was previously bearing on the longitudinal rib 16 is now received and engaged in the recess 17 of the outer sleeve 15, and the annular rim 12 of the ring 10 is received in the longitudinal cut 5 of the inner core 4 of the support 2. The ring 10 is no more coaxial with the needle shield 8. As a consequence, the ring 10 is axially locked in the proximal direction, at least by means of its engagement in said recess 17 and by the abutment of the proximal end 10*a* of the ring 10 against the abutment 17*a* provided in the outer sleeve 15. This can be seen on FIG. 7 on which the longitudinal axis A of the needle shield 8 and the longitudinal axis B of the ring 10 are radially spaced apart. Therefore, the needle shield 8 can not move back in the proximal direction. The needle shield 8 can therefore not move back from its "after use" position to its "in use" position. The ring 10 therefore acts as a locking element of the needle shield 8 and is in a "locking" position when the needle shield 8 is in its "after use" position. In this "locking" position of the ring 10, the ring 10 and the needle shield 8 are decoupled from the helical spring 13 in other words, and in particular because the ring 10 is now axially blocked in the proximal direction, a proximal force exerted on the needle shield 8 will not allow to compress the helical spring 13.

As is visible from FIGS. 1, 5 and 6, in the storage, "before use" and "in use" positions of the needle shield 8, the ring 10 remained coaxial with the needle shield 8 and did not prevent movement of said needle shield 8 from a position to the other. On these FIGS. 1, 5 and 6, the locking element formed by the ring 10 was in a "free" position: on these figures also, the ring 10 and the needle shield 8 are coupled to the helical spring 13.

Figure 8D:
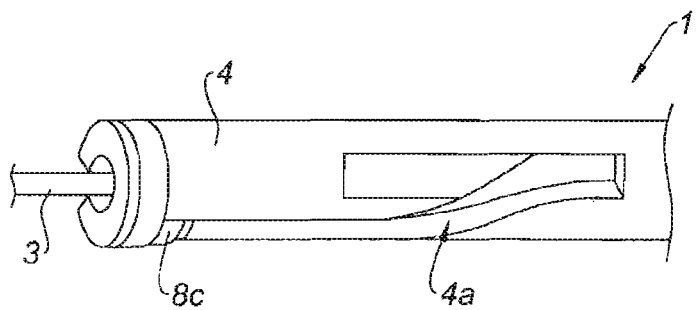

As shown on FIG. 8D, the peg 8*c* now abuts against the free extremity of the second branch of the V-shaped cam 4*a*.

As appears from the description above, the needle 3 is totally free from any contact with the ring 10 when the needle shield 8 moves from its "in use" position to its "after use" position. Indeed, the needle 3 is neither contacted by the needle shield 8 nor by any other part of the assembly 1 during these operations. As a consequence, there is no risk that some liquid optionally present at the distal tip of the needle 3 be spilt around. Moreover, during these operations, the needle 3 is not submitted to any biasing or urging forces, therefore rendering the injection step more reliable.

In the needle protection assembly 1 and the injection device 100 of the invention, the force of the helical spring 13 of the needle protection assembly 1 and the injection device 100 of the invention does not need to be high because it does not have to overcome any flexible locking member. In consequence, when the needle protection assembly 1 and the injection device 100 of the invention are in a "storage" position, as shown on FIG. 1, the force exerted by the helical spring 13 on the different parts forming the needle protection assembly 1 and/or the injection device 100 is not high and does not deform said parts. The helical spring 13 is not cumbersome and the needle protection assembly 1 and/or the injection device 100 can have moderate size. In addition, the helical spring 13 is easy to assemble because it requires less pressure to be compressed than a high force spring.

As previously described, the needle protection assembly 1 of FIGS. 1 to 7 has four positions:
- a "storage" position before in which the needle 3 is protected by the protection cap 200,
- a "before use" position after retrieval of the protection cap 200 and before proper use of the injection device 100, in this "before use" position the needle is at least partly covered by the needle shield 8,
- an "in use" position during which the injection device 100 is applied against the injection site, the needle 3 is inserted in the injection site and a portion of said needle 3 is therefore not covered by the needle shield 8,
- an "after use" position after withdrawal of the needle 3 from the injection site, in this "after use" position, the needle shield 8 covers the needle 3.

In an embodiment not shown, the needle shield may be provided with a cam able to receive therein a peg located on the outer wall of the support, said cam and said peg being able to cooperate so as to define respectively the "before use", the "in use" and the "after use" positions of the needle shield.

In another embodiment not shown, the outer sleeve may be replaced by an inner sleeve received within the needle shield. In such a case, the inner sleeve is provided with a slot in which a part of the wall of the ring becomes engaged in the "after use" position of the needle shield.

In another embodiment not shown, the needle protection assembly may comprise an outer sleeve provided with a longitudinal rib and an inner sleeve provided with a slot, a part of the wall of the ring being engaged in said slot in the "after use" position of the needle shield.

The invention claimed is:

1. Needle protection assembly (1) intended to protect the needle (3) of a needle assembly, said needle protection assembly (1) comprising at least:
   - a support (2) intended to be fixed relative to said needle (3),
   - a needle shield (8) intended to receive at least part of said needle (3), said needle shield (8) having a longitudinal axis A and being axially movable with respect to said support (2) between at least an in use position in which said needle shield (8) is intended to leave a portion of said needle (3) uncovered, and an after use position in which said needle shield (8) is intended to cover said needle (3),
   - an urging member (13) tending to displace said needle shield (8) from said in use position to said after use position, and
   - a locking element (10) intended to prevent said needle shield (8) from moving back from its after use position to its in use position, wherein said locking element (10) has a longitudinal axis B and is radially movable with respect to said needle shield (8) between at least a free position in which the longitudinal axis A of said needle shield (8) and the longitudinal axis B of said locking element (10) are co-axial with each other, and in which said needle shield (8) may be moved from its in use position to its after use position, and a locking position, in which the longitudinal axis B of said locking element (10) is radially spaced apart from and parallel with the longitudinal axis A of said needle shield (8) and in which movement of said needle shield (8) from its after use position to its in use position is prevented, said needle (8) being free from any contact with said locking element (10) at least when said needle shield (8) moves from its in use position to its after use position.

2. Needle protection assembly (1) according to claim 1, wherein said support (2) further comprises an outer sleeve (15) located around said needle shield (8) and said locking element (10), and an inner core (4) received within said needle shield (8) and said locking element (10), said needle shield (8) and said locking element (10) being movable together in translation along said axis A and B with respect to said outer sleeve (15) and to said inner core (4) at least in said in use position of said needle shield (8).

3. Needle protection assembly (1) according to claim 2, further comprising a guiding member (16) intended to maintain said locking element (10) in alignment with said needle shield (8) in said in use position of said needle shield (8) and preventing said locking element (10) to move toward said locking position, and wherein said guiding member is provided on at least one of said inner core (4) or said outer sleeve (15).

4. Needle protection assembly (1) according to claim 3, wherein said guiding member comprises at least a longitudinal rib (16) respectively provided on part of the length of the inner wall of said outer sleeve (15) or on part of the length of the outer wall of said inner core (4), at least part of a wall of said ring (10) bearing on said longitudinal rib (16) in said in use position of said needle shield (8).

5. Needle protection assembly (1) according to claim 4, wherein in said locking position, said locking element (10) is axially locked in the proximal direction, by means of at least part of the proximal end (10*a*) of said locking element (10) resting against at least one abutment (17*a*) provided on said support (2), wherein at least part of said needle shield (8) has the global shape of a tube (8) and at least part of said locking element has the global shape of a ring (10) of radial dimensions substantially similar to that of said at least part of said needle shield having the global shape of a tube (8), and wherein said outer sleeve (15) comprises on its inner wall a recess (17) located in alignment with said longitudinal rib (16), said at least part of a wall of said ring (10) bearing on said longitudinal rib (16) in the in use position of the needle shield (8) being caused to engage said recess (17) by radial displacement of said locking element (10) with respect to said needle shield (8) when said needle shield (8) reaches said after use position under the action of said urging member (13), said recess (17) being provided with said abutment (17*a*).

6. Needle protection assembly (1) according to claim 1, further comprising a directing member (9, 11) designed for causing the radial displacement of said locking element (10) with respect to said needle shield (8) under the action of said urging member (13) when said needle shield (8) reaches said after use position, thereby causing said locking element (10) to move from said free position to said locking position.

7. Needle protection assembly (1) according to claim 6, wherein a first part (11) of said directing member is located on said locking element (10) and a second part (9) of said directing member is located on said needle shield (8), said first and second parts (9, 11) of said directing member cooperating together so as to cause the radial displacement of said locking element (10) with respect to said needle shield (8) under the action of said urging member (13) when said needle shield (8) reaches its after use position.

8. Needle protection assembly (1) according to claim 7, wherein at least part of said needle shield has a global shape of a tube (8) and at least part of said locking element has the global shape of a ring (10) of radial dimensions substantially similar to that of said at least part of said needle shield having a global shape of a tube (8), and wherein said first part of said directing member comprises an angled surface (11) located on the ring (10) and said second part of said directing member comprises a complementary angled surface (9) located on the at least part of said needle shield having a global shape of a tube (8), said angled surface (11) and complementary angled surface (9) being in regard to each other and sliding on each other so as to cause the radial displacement of said locking element (10) with respect to said needle shield (8) under the action of said urging member (13) when said needle shield (8) reaches its after use position.

9. Needle protection assembly (1) according to claim 8, wherein at least one of said angled surface (11) or complementary angled surface (9) is provided with at least one spine (9*a*) extending inwardly and radially, said at least one spine (9*a*) contributing to increase the surface contact between said angled surface (11) and said complementary angled surface (9) when they slide on each other.

10. Needle protection assembly (1) according to claim 1, wherein said needle shield (8) is axially movable with respect to said support (2) between a before use position, in which said needle shield (8) covers at least part of the needle (3), and said in use position.

11. Needle protection assembly (1) according to claim 10, further comprising a cam (4*a*), located on said needle shield (8) or on said support (2), and a peg (8*c*), respectively located on said support (2) or on said shield (8), said cam (4*a*) and said peg (8*c*) being designed so as to cooperate together for defining at least one of said in use position and/or said before use position and/or said after use position of the needle shield (8).

12. Needle protection assembly (1) according to claim 1, wherein in its locking position, said locking element (10) is axially locked in the proximal direction, by means of at least part of the proximal end (10*a*) of said locking element (10) resting against at least one abutment (17*a*) provided on said support (2).

13. Needle protection assembly (1) according to claim 1, wherein said locking element (10) being located between said urging member (13) and said needle shield (8), said locking element (10) and said needle shield (8) are coupled to said urging member (13) when said locking element (10) is in its free position, said locking element (10) and needle shield (8) being decoupled from said urging member (13) when said locking element (10) is in its locking position.

14. Needle protection assembly (1) according claim 1, further comprising a guiding member (16) intended to maintain said locking element (10) in alignment with said needle shield (8) in said in use position of said needle shield (8) and preventing said locking element (10) to move toward said locking position.

15. Needle protection assembly (1) according to claim 1, wherein at least part of said needle shield has the global shape of a tube (8) and at least part of said locking element has the global shape of a ring (10) of radial dimensions substantially similar to that of said at least part of said needle shield having the global shape of a tube (8).

16. Needle protection assembly (1) according to claim 1, wherein said urging member comprises at least a helical spring (13).

17. Needle assembly comprising at least a needle hub provided with a needle (3) further comprising a needle protection assembly (1) according to claim 1.

18. Injection device (100) comprising at least a needle assembly and a reservoir, further comprising a needle protection assembly (1) according to claim 1.

19. Needle protection assembly (1) according to claim 1, further comprising a cam (4a), located on said needle shield (8) or on said support (2), and a peg (8c), respectively located on said support (2) or on said shield (8), said cam (4a) and said peg (8c) being designed so as to cooperate together for defining at least one of said in use position and/or said after use position of the needle shield (8).

* * * * *